United States Patent [19]

Schumann

[11] Patent Number: 5,309,215
[45] Date of Patent: May 3, 1994

[54] PROCEDURE FOR THE DETERMINATION OF PARTICLE SIZE DISTRIBUTION IN PARTICLE MIXTURES

[76] Inventor: Matthias Schumann, Brennerstrasse 1,, 0-5300 Weimar, Fed. Rep. of Germany

[21] Appl. No.: 894,013

[22] Filed: Jun. 5, 1992

[30] Foreign Application Priority Data

Jun. 7, 1991 [DE] Fed. Rep. of Germany ....... 4119240

[51] Int. Cl.$^5$ ...................... G01N 15/02; G01N 15/14
[52] U.S. Cl. ........................................ 356/335; 377/11
[58] Field of Search ...................... 356/335; 377/10, 11

[56] References Cited

U.S. PATENT DOCUMENTS 3,676,647  7/1972  Staffin et al. ........................... 377/11

FOREIGN PATENT DOCUMENTS 435570  7/1991  European Pat. Off. ............ 356/335

Primary Examiner—Richard A. Rosenberger
Attorney, Agent, or Firm—Fay, Sharpe, Beall, Fagan, Minnich & McKee

[57] ABSTRACT

A method for automatic particle size analysis of a particle mixture by linear, optoelectronic scanning of a separated particle stream. Particle chord length categories are counted and converted to a particle size distribution. The method takes into account practical considerations such as mixed particle velocities and mixed grain shapes. The exposure time for the linear scanning determines, as a function of the diameter and the velocity of the smallest particle being measured, the number of particles per category size by means of appearance probabilities of recorded chord lengths for corresponding particle sizes. The determination of particle numbers is made using the sequence of the category of the largest particle diameters to the category of the smallest particle diameter, whereby, after each calculation of a particle size category, the number of chord lengths in the length category is corrected.

3 Claims, 1 Drawing Sheet

PROCEDURE FOR THE DETERMINATION OF PARTICLE SIZE DISTRIBUTION IN PARTICLE MIXTURES

BACKGROUND OF THE INVENTION

The invention concerns a procedure for automatic particle size analysis of particle mixtures, specifically with respect to influencing the technical control of producing and processing such mixture.

The determination of particle size distribution of a disperse mixture shall, as a rule, be done quickly and be representative of an overall aggregate. Aside from the known procedures, such as screen analysis and sedimentation, the opto-electronic measuring procedures are gaining more and more importance, since they primarily satisfy requirements concerning automatization capability.

In Patent Specifications DD-WP 260 764 and DD-WP 278 859, procedures are described for the determination of the granulometric condition and/or granulation ratio of grain mixtures, from which a sample is continuously or also intermittently drawn, and where the particles are optically separated and moved, at predetermined, uniform velocity, at right angles, past a CCD line sensor.

In DD-260-764, the particles are scanned, line by line, in chronologically constant succession. The thus signaled widths of the respective particle segments (chords) are classified into categories of different chord lengths. When reaching a set meter number or meter time, the so-called granulation number is ascertained via a calibration function. Involved here is a rapid procedure, by which for each picked-up particle several chord lengths are recorded and included in the evaluation.

With respect to mixtures of narrowly restricted particle sizes, however, this procedure is unsuitable, inasmuch as the selectivity of the calibration function is no longer adequate.

The practical drawbacks of both inventions consist in the requirement for uniform particle velocity during the measuring process. Such condition either requires high technical expenditure, for instance a vacuum measuring cell, or it restricts the measuring area by neglecting the friction, which is admissible only with relatively heavy particles.

The procedure according to DD-WP 260 764 functions only with nearly similar distribution functions and does not provide any information concerning the course of the particle size distribution. Patent specification DD-WP 278-859 requires that each particle is scanned at least once. This results in an extremely high rate of data, which leads to technical measuring problems or which only permits very low throughput of material under test, which prevents on-line operation.

Procedures which are oriented toward more precise evaluation, are based in that static images are produced via opto-electronic devices, which are then evaluated by means of additional costly device elements or mathematical methods.

From DE-PS 2855 583, a procedure is known whereby a sample of a particle mixture drops from an appropriate height and pictures of the particles are recorded during the dropping with a television camera. From the individual, successively projected static images, the surface distribution of the mixture is ascertained on the basis of the measured projection surfaces. Long measuring times preclude wide application.

DESCRIPTION OF THE PREFERRED EMBODIMENT

Object of the invention is a new procedure, capable of being automated, while utilizing known, simple opto-electronic measuring technology, whereby a relatively broad particle size distribution of a mixture can be measured. In addition to a high throughput of material to be tested, concurrently, a high measuring precision is to be achieved.

By means of known, line-by-line opto-electronic scanning of a separated particle stream, registration of chord lengths and assignment of these lengths to certain chord classes, the task according to the invention is solved in that:

a) the particle stream, in a transparent, fluid or gaseous medium, transports itself, through gravitational or added forces through the opto-electronic measuring distance, vertically vis-a-vis parallel-oriented light rays.

b) the exposure time of a scan is smaller than the quotient $d_{min}/(2*v_{min})$ whereby $d_{min}$ represents the diameter and $v_{min}$ the velocity of the smallest particle, c) the chronological distance between two scans should preferably be greater than the quotient $d_{min}/v_{min}$, d) for each particle size to be analyzed, the probability for occurrence of a chord in a given chord class, is calculable or known, and thus, effective with the largest particle class, retroceding to the smallest, the number of the particles can be ascertained through the quotient from measured chord number to occurrence probability, whereby after each ascertained number of particles of a given size, the chord length distribution must be corrected according to the chords which belong to these particles.

The chord classificator has n chord classes with chord class limitations $l_i (i=1 \ldots n)$, in which the measured and corresponding chords are counted and converted to a number-specific particle size distribution by means of the following transformation algorithm.

The conversion is initially done on the basis of the following two assumptions:

a) the mixture to be analyzed consists of spheres b) the spheres have a diameter $d_j$, which corresponds, in each instance, to upper chord class limitations $(d_j = l_i;\ i, j = 1 \ldots n)$.

For this preconceived model-mixture of geometrically defined particles, a Matrix $p_{j,i}$ can be established, which indicates, with which probability, a particle having a diameter of $d_j$, passing through the measuring distance, yields, during the scanning, a chord length of the $i$-$th$ chord class.

Figure 1:
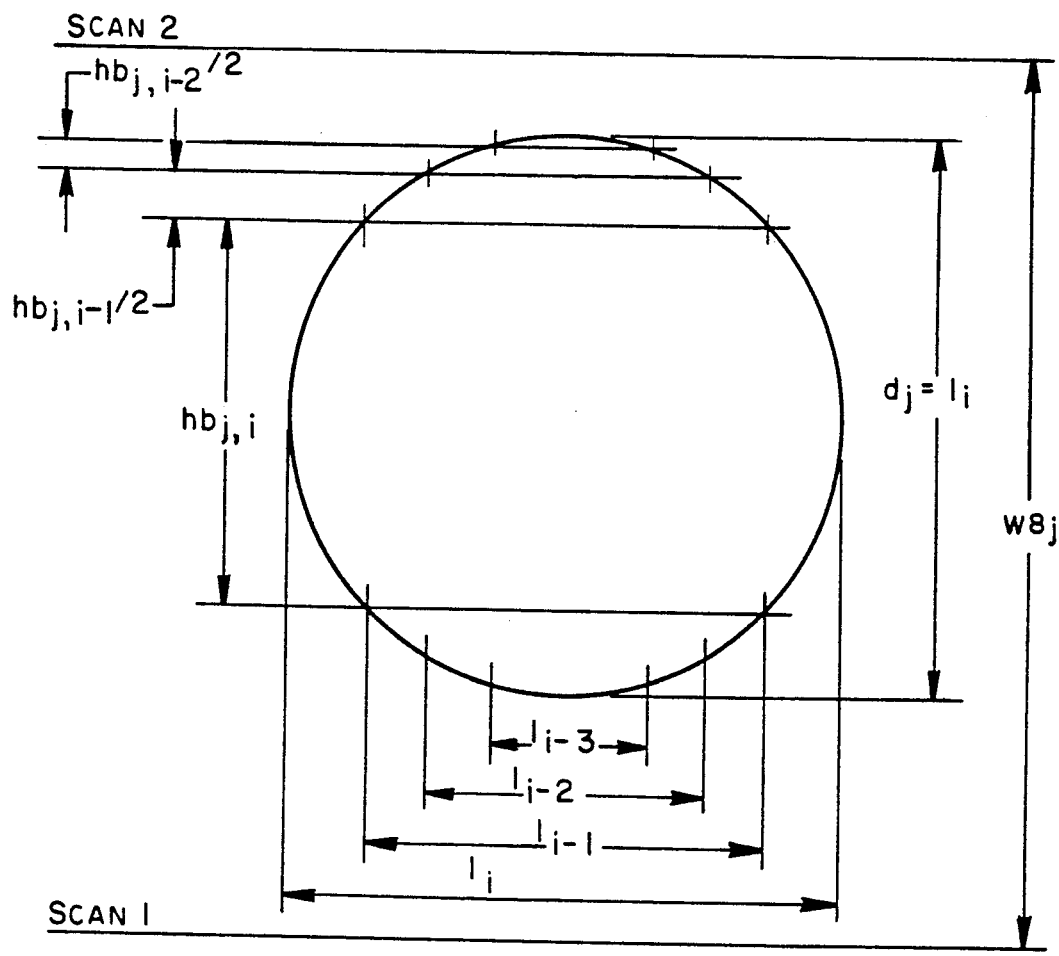
FIG. 1 is a generally diagrammatic view of the preferred chord length measurements.

The probabilities pj, i are calculated from the length ratio $hb_{j,i}/wsj$, whereby $hb_{j,i}$ represents the height of the area within a projected circle, having a diameter of j, wherein chords of longitudinal class i may occur, and $ws_j$ is the travelled distance in the time between two successive scans of a particle having a diameter of j. (FIG. 1). The values for $hb_{j,i}$ can be calculated with known chord class partition, scan frequency and particle velocity.

The calculation is made on the assumption that the particle velocity in the time between two succeeding scans will not experience any relevant change. With the aid of probabilities $p_{j,i}$ and the number of chords $san_i$, recorded in the chord classes, the $pan_j$ number of the particles, beginning with the largest particle diameter $d_j$ can be calculated through the quotient $san_j/p_{j,i}$ ($i=j$).

All chords belonging to these particles in all possible chord classes, taking into consideration the corresponding probabilities, must now be subtracted from the existing chord number distribution. Then, the calculation of the number of particles in the subjacent particle size classes is performed in analog fashion. The obtained number-specific particle size distribution can be transformed into a volume specific distribution and, if bulk density is known, into a mass-specific distribution. In measuring particles with irregular shapes, the model requirements, established for the transformation do not cause any relevant errors.

The measuring process and also the chord length classification and counting are performed by a computer in real time operation. Transformation into a particle size distribution is accomplished by the computer, following the measuring, within tenth of seconds.

Figure 2:
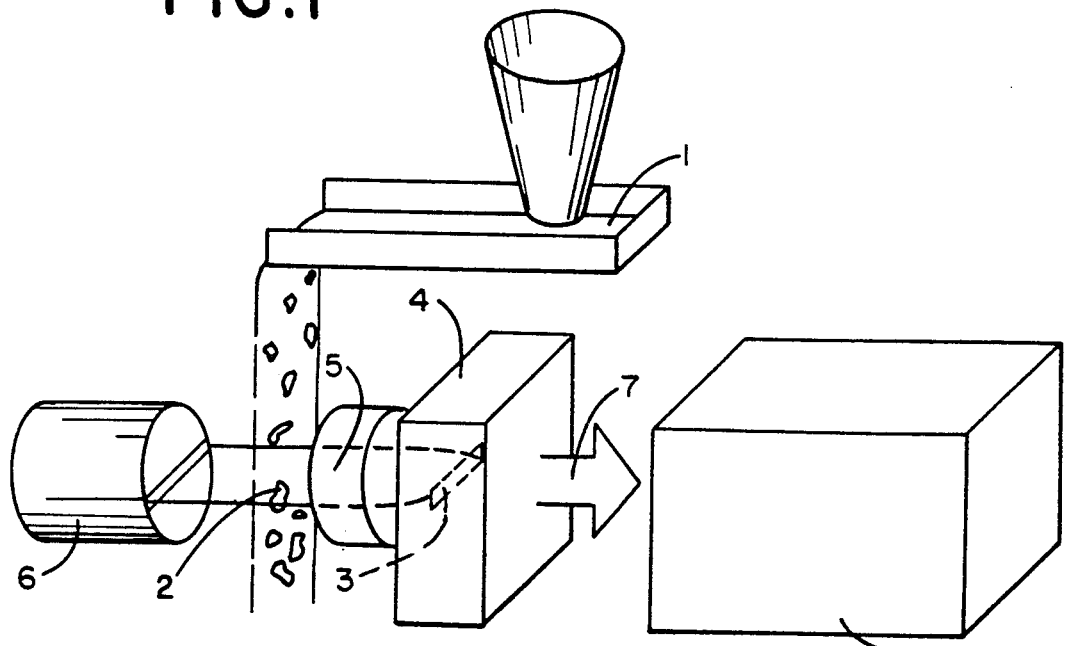
FIG. 2 is a schematic representation to the preferred apparatus.

The invention is explained in more detail using an execution example of the measuring principle illustrated in FIG. 2.

A collective sample, consisting of sand with a grain size from 0.1 to 2 mm, is drawn by means of a conveyor organ 1, from a sample collection container. The conveyor organ can be a conveyor band or a vibration channel, whereby a particle stream, approximately 75 mm wide, is produced, with individual particles separately passing Sensor 3.

With moist and agglomerated measuring material, it is recommended to disperse the sample in a liquid medium, which is then passed alongside the Sensor 3 in horizontal flow.

Sensor 3, a CCD line-sensor, which is arranged within camera 4, having a lens 5, operates synchronous with a pulsed laser diode. The latter transmits via a collimator 6 parallel light with a radiation length of approximately 1 us in constant time intervals of 2 ms.

The chord lengths of some—but not of all—of the particles passing the measuring distance are recorded and assigned to a chord length classificator 7 of a given length class.

With a reproduction ratio of 1:1, a segment of approximately 27 mm width is seized from the 75 mm wide particle stream.

After approximately 10 seconds, the measuring is interrupted. The meter counts of classificator 7 remain intact. The output of the conveyor organ 1 is adjusted to the maximum for the next 10 seconds. After that, the next partial measuring is taken. Such random-sampling-like measuring modus permits sample throughputs from up to 1 kg/min. The subsequent transformation of chord length distribution into a grain size distribution is done in a computer 8.

APPENDIX A

| No. | Chord Length in mm from | to | Chord Number | Particle Diameter in mm | Particle Number | Sum in M % of Particle Size Distribution |
|---|---|---|---|---|---|---|
| 1 | 0,007 | 0,019 | 0 | 0,019 | 0 | 0 |
| 2 | 0,020 | 0,032 | 0 | 0,032 | 0 | 0 |
| 3 | 0,033 | 0,045 | 0 | 0,045 | 0 | 0 |
| 4 | 0,046 | 0,058 | 458.166 | 0.058 | 23.662.246 | 4,37 |
| 5 | 0,059 | 0,084 | 195.910 | 0,084 | 4.266.815 | 6,76 |
| 6 | 0,085 | 0,123 | 150.556 | 0,123 | 1.909.207 | 10.08 |
| 7 | 0,124 | 0,188 | 148.727 | 0,188 | 1.077.269 | 16,75 |
| 8 | 0.189 | 0,266 | 120.341 | 0,266 | 594.504 | 27,16 |
| 9 | 0,267 | 0,383 | 88.727 | 0,383 | 255.582 | 40,49 |
| 10 | 0,384 | 0,565 | 68.743 | 0,565 | 122.457 | 60,96 |
| 11 | 0,566 | 0,838 | 40.128 | 0,838 | 47.357 | 86,78 |
| 12 | 0,839 | 1,228 | 5.889 | 1,228 | 3.987 | 93,61 |
| 13 | 1,229 | 1,800 | 2.325 | 1,800 | 1.004 | 99,03 |
| 14 | 1,810 | 2,632 | 85 | 2,632 | 21 | 99,39 |
| 15 | 2,633 | 3,880 | 38 | 3,880 | 5 | 99,66 |
| 16 | 3,881 | 5,700 | 22 | 5,700 | 2 | 100,00 |
| 17 | 5,701 | 8,378 | 0 | 8,378 | 0 | 100,00 |
| 18 | 8,379 | 12,317 | 0 | 12,317 | 0 | 100,00 |
| 19 | 12,318 | 18,115 | 0 | 18,115 | 0 | 100,00 |
| 20 | 18,116 | 26,630 | 0 | 26,630 | 0 | 100,00 |

What is claimed is:

1. Procedure for determination of particle size distribution of particle mixtures by means of line-by-line opto-electronic scanning of a separated particle stream, whereby chord lengths of the particles are measured and assigned to certain lengths-classes in a classificator, characterized in that
    a) the particle stream moves in a transparent liquid or gaseous medium, by means of gravity or added forces, vertically to a parallel light ray, along the opto-electronic measuring distance,
    b) the exposure time of a scan is smaller than the quotient $d_{min}/(2*v_{min})$ whereby $d_{min}$ constitutes the diameter and $v_{min}$ constitutes the velocity of the smallest to be measured particle,
    c) the chronological interval between two scans is greater than the quotient $d_{min}/v_{min}$
    d) for each particle size to be analyzed, the probabilities for occurrence of a chord in a given chord class are calculable or known and thus, beginning with the largest particle class, retrograde to the smallest, the number of particles are ascertained through the quotient from measured chord number to occurrence probability, whereby after each ascertained number of particles of a given size, the chord length distribution must be corrected in accordance with the chords belonging to these particles.

2. A method for determination of particle size distribution of a particle mixture comprising opto-electronic scanning a particle stream separated from the particle mixture, wherein the particle stream is transported in a transparent fluid or gaseous medium vertically to a parallel ray of light, the chord lengths of particles are measured and assigned to certain length categories, wherein the particles stream for each linear scan by the ray of light is exposed to an exposure time less than the quotient $d_{min}/(2\ v_{min})$, wherein $d_{min}$ stands for the diameter of the smallest particle to be measured and $v_{min}$ stands for the velocity of the smallest particle to be measured, and wherein the number of particles per particle size category is ascertained beginning with the particle size category of the largest particle diameter proceeding to the category with the smallest particle diameter from the quotient of the number of recorded chord lengths in a respective lengths category and the appearance probability of said lengths category for this particular particle size category, whereby after each determination of number of particles in a particle size category the number of chord lengths for those lengths categories which correspond to the not yet determined particle sizes is corrected by the number of those chord lengths, which, according to the appearance probabilities are to be assigned to the particles of the already determined particle size categories.

3. The method of claim 2 wherein said particle size distribution has a minimum diameter of 10 microns.

* * * * *